United States Patent
Chassot et al.

(10) Patent No.: US 6,849,766 B2
(45) Date of Patent: Feb. 1, 2005

(54) 1,4-DIAMINO-2-ALKENYLBENZENE DERIVATIVES, AND DYES CONTAINING THESE COMPOUNDS

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 245 days.

(21) Appl. No.: 10/169,896

(22) PCT Filed: Sep. 10, 2001

(86) PCT No.: PCT/EP01/10408

§ 371 (c)(1),
(2), (4) Date: Jul. 10, 2002

(87) PCT Pub. No.: WO02/057214

PCT Pub. Date: Jul. 25, 2002

(65) Prior Publication Data

US 2003/0121110 A1 Jul. 3, 2003

(30) Foreign Application Priority Data

Jan. 18, 2001 (DE) .......................... 101 02 085

(51) Int. Cl.$^7$ .................. C07F 7/10; C07C 211/52; C07C 211/51; C07C 255/42; A61K 7/13
(52) U.S. Cl. .................. 564/305; 8/408; 8/409; 8/410; 8/411; 8/412; 556/413; 558/418; 564/442; 564/443
(58) Field of Search ................ 556/413; 558/418; 564/305, 442, 443; 8/408, 409, 410, 411, 412

(56) References Cited

U.S. PATENT DOCUMENTS 5,224,965 A * 7/1993 Clausen et al. ............... 8/411
5,292,896 A * 3/1994 Shoshi et al. ................ 549/68

FOREIGN PATENT DOCUMENTS

EP 0 634 163 A 1/1995
EP 0 819 424 A 1/1998

OTHER PUBLICATIONS

"Protective Groups", Organic Synthesis, Kapitel 7, Wiley Interscince, 1991, pp. 305–330.

* cited by examiner

Primary Examiner—Peter G O'Sullivan
(74) Attorney, Agent, or Firm—Michael J. Striker

(57) ABSTRACT

1,4-Diamino-2-alkenylbenzene derivatives of general formula (I) or physiologically tolerated water-soluble salts thereof

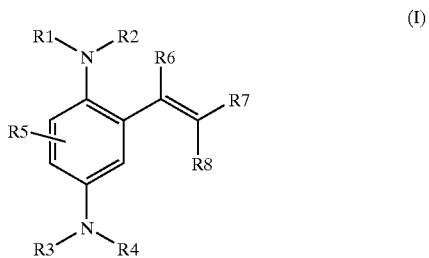

as well as agents for oxidative dyeing of fibers, containing these compounds.

17 Claims, No Drawings

1,4-DIAMINO-2-ALKENYLBENZENE DERIVATIVES, AND DYES CONTAINING THESE COMPOUNDS

BACKGROUND OF THE INVENTION

The invention relates to novel 1,4-diamino-2-alkenylbenzene derivatives and to agents containing these compounds and used for coloring keratin fibers.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diaminopyrazole, and suitable couplers are, for example, resorcinol, 4-chlororesorcinol, 1-naphthol, 3-aminophenol, m-phenylenediamine, 2-amino-4-(2'-hydroxyethyl) aminoanisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

European Patent EP 0 819 424 and European Unexamined Patent Application EP 0 634 163 describe oxidation dyes containing as the developer a 2-alkyl-p-phenylenediamine or a salt thereof, among others.

A need, however, continued to exist for novel developers capable of meeting the requirements for oxidative dye percursors to a major extent.

SUMMARY OF THE INVENTION

Surprisingly, we have now found that novel p-diaminobenzene derivatives of general formula (I) meet the requirements placed on developers to a major degree. In fact, by use of these developers together with most of the known couplers, it is possible to achieve shades of high color intensity that are unusually lightfast and washfast.

Hence, the object of the present invention are 1,4-diamino-2-alkenylbenzene derivatives of general formula (I) or the physiologically tolerated, water-soluble salts thereof

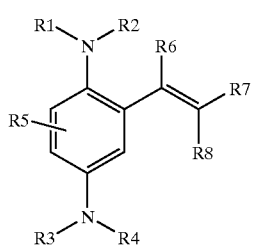

(I)

wherein

R1, R2, R3 and R4 independently of each other denote hydrogen, a $C_1$–$C_6$-alkyl group, $C_2$–$C_4$-hydroxyalkyl group, $C_3$–$C_4$-dihydroxyalkyl group or $C_1$–$C_4$-alkoxy-($C_1$–$C_2$)-alkyl group, or R1 and R2 or R3 and R4 form a four-membered to eight-membered ali-phatic ring, with at least two of the R1 to R4 groups denoting hydrogen;

R5 denotes hydrogen, a halogen atom (F, Cl, Br, I), a $C_1$–$C_4$-alkyl group, a $C_1$–$C_4$-hydroxyalkyl group or a $C_1$–$C_4$-alkoxy group;

R6, R7 and R8 independently of each other denote hydrogen, a halogen atom (F, Cl, Br, I), a cyano group, $C_1$–$C_4$-alkoxy group, $C_1$–$C_6$-alkyl group, —C(O)H group, —Si(CH$_3$)$_3$ group, $C_1$–$C_4$-hydroxyalkyl group, $C_3$–$C_4$-dihydroxyalkyl group, —CH$_2$—Si(CH$_3$)$_3$ group or a group of formula (II)

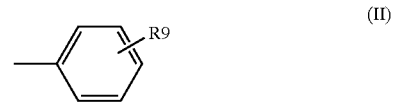

(II)

and R9 denotes hydrogen, an amino group, a halogen atom (F, Cl, Br, I), a nitro group or a hydroxyl group.

Suitable compounds of formula (I) are, for example, the following: 1,4-diamino-2-styrylbenzene; 1,4-diamino-2-propenylbenzene, 1,4-diamino-2-(1-methylpropenyl)benzene; 1,4-diamino-2-(2-methylpropenylbenzene; 1,4-diamino-2-(1,2-dimethylpropenylbenzene; 1-amino-4-methylamino-2-styrylbenzene; 2-(2,5-diaminophenyl)-2-propen-1-ol; 3-(2,5-diaminophenyl)-2-propen-1-ol; 1-amino-4-methylamino-2-(1-methylpropenyl)benzene; 1-amino-4-methylamino-2-(2-methylpropenyl)benzene; 1-amino-4-methylamino-2-(1,2-dimethylpropenyl)benzene; 1-amino-4-(2-hydroxyethyl)amino-2-stryrylbenzene; 1-amino-4-(2-hydroxyethyl)amino-2-propenyl-benzene; 1-amino-4-(2-hydroxyethyl)amino-2-(1-methylpropenyl)benzene;1-amino-4-(2-hydroxyethyl)amino-2-(2-methylpropenyl)benzene; 1-amino-4-(2-hydroxyethyl)-amino-2-(1,2-dimethylpropenyl)benzene, 1-amino-4-di(2-hydroxyethyl)amino-2-styrylbenzene; 1-amino-4-di(2-hydroxyethyl)amino-2-propenylbenzene; 1-amino-4-di(2-hydroxyethyl)amino-2-(1-methylpropenyl)benzene; 1-amino-4-di(2-hydroxyethyl)amino-2-(2-methylpropenyl) benzene and 1-amino-4-di(2-hydroxyethyl)amino-2-(1,2-dimethylpropenyl)benzene.

Preferred compounds of formula (I) are those wherein (i) one or more of the R5, R6, R7 and R8 groups denote hydrogen and/or (ii) R1, R2, R3 and R4 all denote hydrogen at the same time and/or (iii) one or more of the R6, R7 and R8 groups denote $C_1$–$C_4$-alkyl or $C_1$–$C_4$-hydroxyalkyl.

In particular, the following compounds are to be mentioned: 1,4-diamino-2-stryrylbenzene; 1,4-diamino-2-propenylbenzene; 1,4-diamino-2-(1-methylpropenyl)benzene; 1,4-diamino-2-(2-methylpropenyl)benzene; 1,4-diamino-2-(1,2-dimethylpropenyl)benzene; 1,4-diamino-2-propenylbenzene; 2-(2,5-diaminophenyl)-2-propen-1-ol; 3-(2,5-diaminophenyl-2-propen-1-ol and 3-(2,5-diaminophenyl)-2-propen-1-ol [sic-Translator].

The 1,4-diamino-2-alkenylbenzene derivatives of formula (I) can be used as free bases or in the form of their physiologically tolerated salts with inorganic or organic acids, for example hydrochloric acid, sulfuric acid, phosphoric acid, acetic acid, propionic acid, lactic acid or citric acid.

The 1,4-diamino-2-alkenylbenzene derivatives of formula (I) can be prepared by known methods of synthesis. For example, the synthesis of the compounds of the invention can be carried out as follows: a) by tetrakis (triphenylphosphine)palladium(O)-catalyzed coupling of a substituted benzene of formula (III)

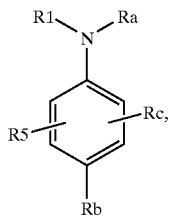

(III)

with a compound of formula (IV)

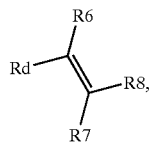

(IV)

wherein
Ra denotes a protective group, as described, for example, in the chapter on "Protective Groups" in Organic Synthesis, chapter 7, Wiley Interscience, 1991,
Rb denotes NR1Ra or NO$_2$,
Rc denotes halogen, and Rd denotes B(OH)$_2$, or Rc denotes B(OH)$_2$ and Rd denotes halogen, and
R1, R5, R6, R7 and R8 have the same meaning as in formula (I), followed by removal of the protective group or by removal of the protective group and reduction of the nitro group;
or b) by a tetrakis(triphenylphosphine)palladium(O)-catalyzed coupling of a substituted benzene of formula (V)

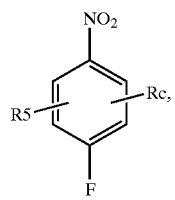

(V)

with the aforesaid compound of formula (IV) [the Rc, Rd, R5, R6, R7 and R8 groups having the same meaning as in formulas I) and (IV)];
followed by substitution of the resulting substituted benzene of formula (VI)

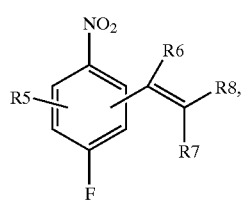

(VI)

with an amine of formula HNR1R2,
wherein R1, R2 have the same meaning as in formula (I), followed by reduction of the nitro group.

The 1,4-diamino-2-alkenylbenzene derivatives of formula (I) are readily water-soluble and produce shades of high color intensity and excellent color fastness, particularly in terms of light fastness, wash fastness and rubbing fastness. The compounds of formula (I) also show outstanding storage stability, particularly as constituents of the colorants described in the following.

Hence, another object of the present invention are agents for oxidative dyeing of keratin fibers, for example hair, furs, feathers or wool, particularly human hair, based on a developer-coupler combination containing as the developer at least one 1,4-diamino-2-alkenylbenzene derivative of formula (I).

The colorant of the invention contains the 1,4-diamino-2-alkenylbenzene derivative of formula (I) in an amount from about 0.005 to 20 wt. %, an amount of about 0.01 to 5.0 wt. % and especially 0.1 to 2.5 wt. % being particularly preferred.

Preferred couplers are: N-(3-dimethylaminophenyl)urea, 2,6-diaminopyridine, 2-amino-4-[(2-hydroxyethyl)amino] anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di (2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]-aniline, 1,3-di(2,4-diaminophenoxy)propane, di(2,4-diaminophenoxy) methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl) amino]-4-methoxy-2-methylphenol, 5-[(2-hydroxyethyl) amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy) ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4- dihydro-1,4 [2H]benzoxazine, 3-methyl-1-phenyl-5-pyrazolone, 5,6-di-hydroxyindole, 5,6-dihydroxyindoline, 5-hydroxyindole, 6-hydroxyindole, 7-hydroxyindole and 2,3-indolinedione.

Although, because of the advantageous properties of the 1,4-diamino-2-alkenylbenzene derivatives of formula (I) described herein, it would be obvious to use them as the only developers, it is, of course, also possible to use the 1,4-diamino-2-alkenylbenzene derivatives of formula (I) together with known developers, for example 1,4-diaminobenzene, 2,5-diaminotoluene, 2,5-diaminophenylethyl alcohol, 4-aminophenol and the derivatives thereof, for example 4-amino-3-methylphenol, 4,5-diamino-1-(2-hydroxyethyl)pyrazole,4,5-diamino-1-benzylpyrazole,4,5-diamino-1-(4-meth-ylbenzyl)pyrazole or the tetraaminopyrimidines.

The couplers and developers can be present in the colorant of the invention either individually or in admixture with one another, the total amount of couplers and developers in the colorant of the invention being about 0.005 to 20 wt. % preferably about 0.01 to 5.0 wt. % and particularly 0.1 to 2.5 wt. % (based on the total amount of colorant).

The total amount of the developer-coupler combination contained in the colorant described herein is preferably about 0.01 to 20 wt. %, an amount of about 0.02 to 10 wt. % and especially 0.2 to 6.0 wt. % being particularly preferred. In general, the developer and the coupler are used in approximately equimolar amounts; however, it is not disadvantageous if the developer is present in a certain excess or deficiency.

Moreover, the colorant of the invention can also contain other dye components, for example 6-amino-2-methylphenol and 2-amino-5-methylphenol, as well as common direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.] 42 510) and 4-[(4'-amino-3'-methylphenyl)-(4"-imino-3"-methyl-2",5"-cyclohexadien-1"-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino]-4-nitrobenzene, azo dyes such as, for example, sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain these dyes in an amount from about 0.1 to 4.0 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants are to be used for coloring hair, they can contain other common cosmetic additives, for example antioxidants such as ascorbic acid, thio-glycolic acid or sodium sulfite, as well as perfume oils, complexing agents, wetting agents, emulsifiers, thickeners and hair-care agents. The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5.0 wt. %.

Depending on the composition, the colorant of the invention can be weakly acidic, neutral or alkaline. In particular, it has a pH of about 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 1,4-diamino-2-alkenylbenzene derivative of formula (I) as developer give hair colorations of excellent color fastness, particularly in terms of light fastness, wash fastness and rubbing fastness. As far as the dyeing properties are concerned, the hair colorants of the invention provide a wide range of different color shades from blond to brown, purple, violet and even blue and black, depending on the kind and composition of the dye components. These color shades are unusually intense. The very good coloring properties of the hair colorant of the present invention also manifest themselves in that these colorants make it possible to dye gray keratin fibers, particularly gray human hair, previously not damaged chemically, without any problems and with good covering power.

The following examples illustrate the object of the invention in greater detail without limiting its scope.

EXAMPLES

Example 1

Synthesis of 2,5-diamino-1-(ethenyl)benzenes.
(General Method of Synthesis)

A. Synthesis of N,N'-bis(tert.butoxycarbonyl)-2,5-diamino-1-phenylboric acid

N,N'-bis(tert.butoxycarbonyl)-2,5-diamino-1-phenylboricacid is obtained by reaction of N,N'-bis(tert.butoxycarbonyl)-2,5-diamino-1-bromobenzene with tert.butyllithium and trimethyl borate by the method described by J. M. Tour and J. J. S. Lamba in J. Am. Chem. Soc. 1994, 116, page 11723.

B. Synthesis of 2,5-diamino-1-vinylbenzenes 0.035 g (0.0001 mole) of N, N'-bis(tert.-butoxycarbonyl)-2,5-diamino- 1-phenylboric acid and 0.00015 mole of the corresponding bromo derivative were dissolved in 10 mL of 1,2-dimethoxyethane under argon. Then, 0.005 g of tetrakis (triphenylphosphine)palladium (0.000005 mole) and 0.13 mL of a 2-normal potassium carbonate solution were added, and the reaction mixture was heated to 80° C. At the end of the reaction, the reaction mixture was poured into 10 mL of ethyl acetate, and the organic phase was extracted with dilute sodium hydroxide solution and then dried over magnesium sulfate. The solvent was distilled off in a rotary evaporator, and the residue was purified on silica gel with petroleum ether/ethyl acetate (9:1). The product thus obtained was dissolved in 4 mL of ethanol and heated to 50° C. To prepare the hydrochloride, 1.5 mL of a 2.9-molar ethanolic hydrochloric acid solution was added dropwise. The precipitate was filtered off, washed twice with 1-mL portions of ethanol and then dried.

a. 1.4-Diamino-2-propenylbenzene hydrochloride
Bromo derivative used: 1-propenyl bromide
Yield: 0.015 g (94% of the theoretical) Mass spectrum: MH⁺ 149(100)

b. 1,4-Diamino-2-(1-methylpropenyl)benzene hydrochloride
Bromo derivative used: 1-bromo-1-methylpropene
Yield: 0.015 g (95% of the theoretical) Mass spectrum: MH⁺ 163(100)

c. 1,4-Diamino-2-(2-methylpropenyl)benzene hydrochloride
Bromo derivative used: 1-bromo-2-methyl-1-propene
Yield: 0.012 g (90% of the theoretical) Mass spectrum: MH⁺ 163(100)

d. 1,4-Diamino-2-(1,2-dimethylpropenyl)benzene hydrochloride
Bromo derivative used: 1-bromo-1,2-dimethyl-1-propene
Yield: 0.012 g (80% of the theoretical) Mass spectrum: MH⁺ 176(100)

e. 1,4-Diamino-2-stryrylbenzene hydrochloride
Bromo derivative used: 1-bromo-2-phenylethylene
Yield: 0.025 g (90% of the theoretical) Mass spectrum: M⁺ 210(10) [sic-Translator]

Examples 2 to 6

Hair Colorants

Hair colorant solutions having the following composition were prepared:

| | |
|---|---|
| 1.25 mmoles | of developer of formula (I) according to Table 1 |
| 1.25 mmoles | of coupler according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Coupler | | | |
|---|---|---|---|---|---|
| Example No. | Developer of Formula (I) as per | I 1,3-dihydroxybenzene | II 1,3-diamino-4-(2-hydroxyethoxy)benzene sulfate | III 5-amino-2-methylphenol | IV 1-naphthol |
| 2. | Example 1a | dark-blond | dark-blue | purple | blue |
| 3. | Example 1b | dark-blond | dark-blue | purple | blue |
| 4. | Example 1c | dark-blond | blue-gray | purple | blue |
| 5. | Example 1d | blond | blue-gray | purple | blue |
| 6. | Example 1e | blond | blue | purple | blue |

Examples 7 to 26

Hair Colorants

Hair colorant solutions of the following composition were prepared:

| | |
|---|---|
| X g | of 1,4-diamino-2-alkenylbenzene derivative of formula (I) (developer E1 or E2 as per Table 2) |
| U g | of developer E8 to E15 as per Table 2 |
| Y g | of coupler K11 to K36 as per Table 4 |
| Z g | of direct dye D1 to D3 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 5 shows the coloring results.

Examples 27 to 38

Hair Colorants

Dye carriers in cream form and having the following composition were prepared:

```
    X g   of 1,4-diamino-2-alkenylbenzene derivative of formula (I)
          (developer E1 or E2 as per Table 2)
    U g   of developer E8 to E15 as per Table 2
    Y g   of coupler K11 to K36 as per Table 4
    Z g   of direct dye D2 as per Table 3
 15.0 g   of cetyl alcohol
  0.3 g   of ascorbic acid
  3.5 g   of sodium lauryl alcohol diethylene glycol ether sulfate,
          28% aqueous solution
  3.0 g   of ammonia, 22% aqueous solution
  0.3 g   of sodium sulfite, anhydrous
to 100 g  water
```

Just before use, 30 g of the foregoing coloring cream was mixed with 30 g of a 6% aqueous solution of hydrogen peroxide. The mixture was then applied to the hair. After an exposure time of 30 min at 40° C., the hair was rinsed with water, washed with a commercial shampoo and dried. The coloring results are presented in Table 6.

Unless otherwise indicated, all percentages in the present application are by weight.

TABLE 2

Developers

| | |
|---|---|
| E1 | 1,4-diamino-2-propenylbenzene hydrochloride |
| E2 | 1,4-diamino-2-(1,2-dimethylpropenyl)benzene hydrochloride |
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

Direct Dyes

| | |
|---|---|
| D1 | 2,6-diamino-3-[(3-pyridinyl)azo]pyridine |
| D2 | 6-chloro-2-ethylamino-4-nitrophenol |
| D3 | 2-amino-6-chloro-4-nitrophenol |

TABLE 4

Couplers

| | |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene hydrochloride |

TABLE 4-continued

Couplers

| | |
|---|---|
| K35 | 3,4-methylenedioxyphenol |
| K36 | 2-amino-5-methylphenol |

TABLE 5

Hair Colorants

| | Example No. | | | |
|---|---|---|---|---|
| | 7 | 8 | 9 | 10 |
| Dyes | (Dyes in grams) | | | |
| E1 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Coloring results | red-brown | red-brown | red-brown | red-brown |

| | Example No. | | | | | |
|---|---|---|---|---|---|---|
| | 11 | 12 | 13 | 14 | 15 | 16 |
| Dyes | (Dyes in grams) | | | | | |
| E1 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring result | blond | blond | blond | blond | blond | blond |

| | Example No. | | | |
|---|---|---|---|---|
| | 17 | 18 | 19 | 20 |
| Dyes | (Dyes in grams) | | | |
| E2 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Coloring result | red-brown | red-brown | red-brown | red-brown |

| | Example No. | | | | | |
|---|---|---|---|---|---|---|
| | 21 | 22 | 23 | 24 | 25 | 26 |
| Dyes | (Dyes in grams) | | | | | |
| E2 | 0.35 | 0.25 | 0.30 | 0.10 | 0.10 | 0.15 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |

TABLE 5-continued

Hair Colorants

| | | | | | | |
|---|---|---|---|---|---|---|
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring result | blond | blond | blond | blond | blond | blond |

TABLE 6

Hair Colorants

| | Example No. | | | | | |
|---|---|---|---|---|---|---|
| | 27 | 28 | 29 | 30 | 31 | 32 |
| Dyes | | | (Dyes in grams) | | | |
| E1 | 1.80 | 1.80 | 1.80 | 0.70 | 0.70 | 0.70 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Coloring results | black | black | black | brown | brown | brown |

| | Example No. | | | | | |
|---|---|---|---|---|---|---|
| | 33 | 34 | 35 | 36 | 37 | 38 |
| Dyes | | | (Dyes in grams) | | | |
| E1 | 2.00 | 2.00 | 2.00 | 0.80 | 0.80 | 0.80 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Coloring results | black | black | black | brown | brown | brown |

What is claimed is:

1. A 1,4-diamino-2-alkenylbenzene derivative of formula (I), or a physiologically tolerated, water-soluble salt thereof,

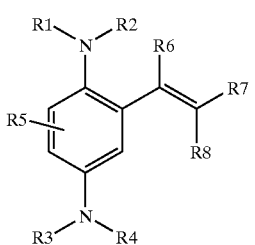

(I)

wherein R1, R2, R3 and R4 independently of each other denote hydrogen, a $C_1$–$C_6$-alkyl group, a $C_2$–$C_4$-hydroxyalkyl group, a $C_3$–$C_4$-dihydroxyalkyl group or a $C_1$–$C_4$-alkoxy-($C_1$–$C_2$)-alkyl group, or R1 and R2 or R3 and R4 form a four-membered to eight-membered aliphatic ring, with at least two of said R1, R2, R3 and R4 groups denoting hydrogen;

R5 denotes hydrogen, a halogen atom, a $C_1$–$C_4$-alkyl group, a $C_1$–$C_4$-hydroxyalkyl group or a $C_1$–$C_4$-alkoxy group;

R6, R7 and R8, independently of each other, denote hydrogen, a halogen atom, a cyano group, a $C_1$–$C_4$-alkoxy group, a $C_1$–$C_6$-alkyl group, —C(O)H, —Si(CH$_3$)$_3$, a $C_1$–$C_4$-hydroxyalkyl group, a $C_3$–$C_4$-dihydroxyalkyl group, —CH$_2$—Si(CH$_3$)$_3$ or an aromatic group of formula (II):

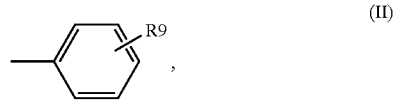

(II)

and

R9 denotes hydrogen, an amino group, a halogen atom, a nitro group or a hydroxyl group.

2. The 1,4-diamino-2-alkenylbenzene derivative of formula (I) or the physiologically tolerated, water-soluble salt thereof, as defined in claim 1, wherein said halogenatom is F, Cl, Br or I.

3. The 1,4-diamino-2-alkenylbenzene derivative of formula (I), or the physiologically tolerated, water-soluble salt thereof, as defined in claim 1, wherein at least one of said R5, R6, R7 and R8 is hydrogen.

4. The 1,4-diamino-2-alkenylbenzene derivative of formula (I), or the physiologically tolerated, water-soluble salt thereof, as defined in claim 1, wherein said R1, said R2, said R3 and said R4 are each hydrogen.

5. The 1,4-diamino-2-alkenylbenzene derivative of formula (I), or the physiologically tolerated, water-soluble salt thereof, as defined in claim 1, wherein at least one of said R6, R7 and R8denote a $C_1$–$C_4$-alkyl group or a $C_1$–$C_4$-hydroxyalkyl group.

6. A 1,4-diamino-2-alkenylbenzene derivative selected from the group consisting of 1,4-diamino-2-styrylbenzene, 1,4-diamino-2-propenylbenzene, 1,4-diamino-2-(1-methylpropenyl)benzene, 1,4-diamino-2-(2-methylpropenyl)-benzene, 1,4-diamino-2-(1,2-dimethylpropenyl)benzene, 1,4-diamino-2-propenylbenzene, 2-(2,5-diaminophenyl)-2-propen-1-ol, 3-(2,5-diaminophenyl)-2-propen-1-ol and 3-(2,5-diaminophenyl)-2-propen-1-ol; or a physiologically tolerated water-soluble salt thereof.

7. The 1,4-diamino-2-alkenylbenzene derivative of formula (I), or the physiologically tolerated, water-soluble salt thereof, as defined in claim 1, consisting of said water-soluble salt and wherein said water-soluble salt is a salt of hydrochloric acid, sulfuric acid, phosphoric acid, acetic acid, propionic acid, lactic acid or citric acid.

8. An agent of oxidative dyeing of keratin fibers, said agent comprising a combination of at least one coupler and at least one developer, wherein said at least one developer comprises 1,4-diamino-2-alkenylbenzene derivative of formula (I), or a physiologically tolerated, water-soluble salt thereof,

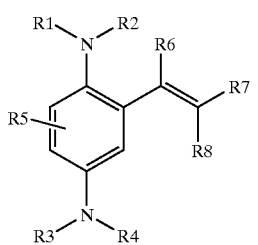

(I)

wherein R1, R2, R3 and R4, independently of each other, denote hydrogen, a $C_1$–$C_6$-alkyl group, a $C_2$–C4-hydroxyalkyl group, a $C_3$–C4-dihydroxyalkyl group or a C$_1$–C$_4$-alkoxy-(C$_1$–C$_2$)-alkyl group, or R1 and R2 or R3 and R4 form a four-membered to eight-membered aliphatic ring, with at least two of said R1, R2, R3 and R4 representing hydrogen;

R5 denotes hydrogen, a halogen atom, a C$_1$–C$_4$-alkyl group, a C$_1$–C$_4$-hydroxyalkyl group or a C$_1$–C$_4$-alkoxy group;

R6, R7 and R8, independently of each other, denote hydrogen, a halogen atom, a cyano group, a C$_1$–C$_4$-alkoxy group, a C$_1$–C$_6$-alkyl group, —C(O)H, —Si(CH$_3$)$_3$, a C$_2$–C4-hydroxyalkyl group, a C$_3$–C$_4$-dihydroxyalkyl group, —CH$_2$—Si(CH$_3$)$_3$ or an aromatic group of formula (II):

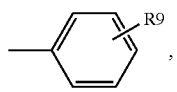

and

R9 denotes hydrogen, an amino group, a halogen atom, a nitro group or a hydroxy group.

9. The agent as defined in claim 8, wherein said 1,4-diamino-2-alkenylbenzene derivative is at least one member selected from the group consisting of 1,4-diamino-2-styrylbenzene, 1,4-diamino-2-propenylbenzene, 1,4-diamino-2-(1-methylpropenyl)benzene, 1,4-diamino-2-(2-methylpropenyl)benzene, 1,4-diamino-2-(1,2-dimethylpropenyl)benzene, 1,4-diamino-2-propenylbenzene, 2-(2,5-diaminophenyl)-2-propen-1-ol, 3-(2,5-diaminophenyl)-2-propen-1-ol and 3-(2,5-diaminophenyl)-2-propen-1-ol.

10. The agent as defined in claim 8, containing from 0.005 to 20.0 percent by weight of said 1,4-diamino-2-alkenylbenzene derivative of formula (I), or said physiologically tolerated, water-soluble salt thereof.

11. The agent as defined in claim 8, containing from 0.005 to 20 percent by weight of said at least one coupler and said at least one developer.

12. The agent as defined in claim 8, wherein said at least one developer includes at least one member selected from the group consisting of 1,4-diaminobenzene, 2,5-diaminotoluence, 2-(2,5-diaminophenyl)ethyl alcohol, 4-aminophenol, 4-aminophenol derivatives, 4,5-diaminopyrazole derivatives and tetraaminopyrimidines.

13. The agent as defined in claim 8, further comprising at least one direct-dyeing dye compound.

14. The agent as defined in claim 8, having a pH of from 6.5 to 11.5.

15. The agent as defined in claim 8, wherein said at least one coupler is selected from the group consisting of 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethyoxybenzene, 2,3-diamino-6-methoxypyridine, 3-amiono-6-methoxy-2-(methylamino)pyridine, 2,6-diamino-3,5-dimethoxypyridine, 3,5-diamino-2,6-dimethoxypyrindine, 1,3-diaminobenzene, 2,4-diamino-1-(2-hydroxyethoxy)benzene, 2,4-diamino-1,5-di(2-hydroxyethoxy)-benzene, 1-(2-aminoethoxy)-2,4-diaminobenzene, 2-amino-1-(2-hydroxy-ethoxy)-4-methylaminobenzene, 2,4-diaminophenoxyacetic acid, 3-[(di(2-hydroxyethyl)amino]aniline, 4-amino-2-di[2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminphenoxy)methane, 1,3-diamino-2,4-dimethoxybenzene, 2,6-bis-(2-hydroxyethyl)aminotoluene, 4-hydroxyindole, 3-dimethylamoinophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethtyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

16. The agent as defined in claim 8, and in the form of an aqueous solution, an aqueous-alcoholic solution, a cream, a gel or an emulsion.

17. The agent as defined in claim 16, consisting of a hair colorant and including at least one cosmetic additive ingredient selected from the group consisting of lower aliphatic alcohols, cationic surfactants, anionic surfactants, amphoteric surfactants, nonioinic surfactants, thickeners, and hair care agents.

* * * * *